US012809490B2

(12) United States Patent
Poulin

(10) Patent No.: US 12,809,490 B2
(45) Date of Patent: Nov. 24, 2026

(54) ASSISTANCE IN RESPONSE TO PREDICTIONS IN CHANGES OF PSYCHOLOGICAL STATE

(71) Applicant: Christian D. Poulin, Portsmouth, NH (US)

(72) Inventor: Christian D. Poulin, Portsmouth, NH (US)

(73) Assignee: Poulin Holdings, LLC, Portsmouth, NH (US)

( * ) Notice: Subject to any disclaimer, the term of this patent is extended or adjusted under 35 U.S.C. 154(b) by 1089 days.

(21) Appl. No.: 16/985,518

(22) Filed: Aug. 5, 2020

(65) Prior Publication Data

US 2021/0045696 A1 Feb. 18, 2021

Related U.S. Application Data

(60) Provisional application No. 62/886,519, filed on Aug. 14, 2019.

(51) Int. Cl.
*G06F 3/048* (2013.01)
*A61B 5/00* (2006.01)
(Continued)

(52) U.S. Cl.
CPC .............. *G06F 3/048* (2013.01); *A61B 5/165* (2013.01); *A61B 5/7264* (2013.01);
(Continued)

(58) Field of Classification Search
CPC ........ G06N 20/00; G06N 5/04; G06F 19/345; G06F 3/048; G06F 16/9577;
(Continued)

(56) References Cited

U.S. PATENT DOCUMENTS 8,930,178 B2 1/2015 Pestian et al.
9,817,949 B2 * 11/2017 Poulin .................... G16H 50/20
(Continued)

FOREIGN PATENT DOCUMENTS

WO WO-2004003818 A2 * 1/2004 ............. G16H 40/67
WO WO-2019246239 A1 * 12/2019 ............. A61B 5/164

OTHER PUBLICATIONS

Alambo et al., "Question Answering for Suicide Risk Assessment using Reddit" Mar. 14, 2019, IEEE, pp. 468-473. (Year: 2019).*
(Continued)

*Primary Examiner* — Chase P. Hinckley
(74) *Attorney, Agent, or Firm* — Fish & Richardson P.C.

(57) ABSTRACT

Computer implemented techniques for classifying mental states of individuals and providing tailored support are described. The techniques determine sets of features that are associated with multiple groups having different mental status, and a classification model is used to classify one group against another group. The techniques also include receiving user set goal, querying a system database to determine whether there is a machine learning model to predict risk associated with the received goal assessing changes in a real-time risk value associated with the goal, generating an automated dialog associated with assessed changes in a real-time risk value associated with the goal, posting to a buddy system the real time risk value with the generated dialog, tracking edits made on the buddy system, and finally a comparison of users and their assisted goal accomplishment.

20 Claims, 8 Drawing Sheets

(51) Int. Cl.

| | |
|---|---|
| *A61B 5/16* | (2006.01) |
| *A61N 5/06* | (2006.01) |
| *G06F 16/3329* | (2025.01) |
| *G06F 16/957* | (2019.01) |
| *G06N 20/00* | (2019.01) |
| *G06Q 10/40* | (2026.01) |
| *G06Q 50/22* | (2018.01) |
| *G16H 20/70* | (2018.01) |

(52) U.S. Cl.
CPC .......... *A61B 5/7267* (2013.01); *A61B 5/7275* (2013.01); *A61B 5/746* (2013.01); *A61N 5/0618* (2013.01); *G06F 16/33295* (2025.01); *G06F 16/9577* (2019.01); *G06N 20/00* (2019.01); *G06Q 10/40* (2026.01); *G06Q 50/22* (2013.01); *G16H 20/70* (2018.01)

(58) Field of Classification Search
CPC . G06F 16/33295; A61B 5/7275; A61B 5/165; A61B 5/7267; A61B 5/7264; A61B 7/46; G06Q 50/22; G06Q 10/40; G16H 20/70; A61N 5/0618
See application file for complete search history.

(56) References Cited

U.S. PATENT DOCUMENTS

| | | | | |
|---|---|---|---|---|
| 10,043,591 | B1 * | 8/2018 | LaBorde | G06N 3/08 |
| 10,388,410 | B1 * | 8/2019 | LaBorde | G16H 50/70 |
| 10,650,920 | B2 * | 5/2020 | Moturu | G16H 15/00 |
| 10,812,424 | B1 * | 10/2020 | Bommaraju | G06N 20/00 |
| 10,860,805 | B1 * | 12/2020 | Coppersmith | G06F 40/216 |
| 11,200,885 | B1 * | 12/2021 | Mandal | G06F 40/279 |
| 2003/0158467 | A1 | 8/2003 | Liebert | |
| 2003/0180698 | A1 | 9/2003 | Salerian | |
| 2005/0071198 | A1 | 3/2005 | Krupa | |
| 2006/0122472 | A1 | 6/2006 | Pullman | |
| 2006/0150989 | A1 | 7/2006 | Migaly | |
| 2006/0206293 | A1 * | 9/2006 | Poulin | G06F 40/30 703/2 |
| 2007/0112585 | A1 | 5/2007 | Breiter et al. | |
| 2008/0154821 | A1 * | 6/2008 | Poulin | G06Q 10/0631 706/21 |
| 2009/0240522 | A1 | 9/2009 | Handal | |
| 2010/0088262 | A1 | 4/2010 | Visel et al. | |
| 2011/0118555 | A1 | 5/2011 | Dhumne et al. | |
| 2011/0213557 | A1 * | 9/2011 | Kopta | G16H 10/20 702/19 |
| 2013/0325491 | A1 * | 12/2013 | Ferrari | G16H 40/63 705/2 |
| 2014/0222719 | A1 * | 8/2014 | Poulin | G16Z 99/00 706/46 |
| 2014/0245207 | A1 * | 8/2014 | Poulin | G06F 18/2111 715/771 |
| 2015/0033120 | A1 | 1/2015 | Cooke et al. | |
| 2017/0064240 | A1 * | 3/2017 | Mangat | G06F 16/9535 |
| 2017/0300643 | A1 * | 10/2017 | Bezark | G06Q 40/08 |
| 2018/0096740 | A1 * | 4/2018 | Moturu | G16H 15/00 |
| 2019/0034494 | A1 * | 1/2019 | Bradley | G06Q 10/0637 |
| 2019/0115027 | A1 * | 4/2019 | Shah | G10L 17/22 |
| 2019/0117143 | A1 * | 4/2019 | Fedor | A61B 5/165 |
| 2019/0239791 | A1 * | 8/2019 | Beck | A61B 5/165 |
| 2019/0258714 | A1 * | 8/2019 | Zhong | G06N 3/084 |
| 2019/0267112 | A1 * | 8/2019 | Taliaz | G16H 10/60 |
| 2019/0286540 | A1 * | 9/2019 | Bates | G06F 18/23 |
| 2019/0385051 | A1 * | 12/2019 | Wabgaonkar | G06N 3/084 |
| 2019/0385711 | A1 * | 12/2019 | Shriberg | G09B 19/00 |
| 2019/0385748 | A1 * | 12/2019 | Thomas | G06N 3/08 |
| 2020/0082927 | A1 * | 3/2020 | Hernandez | A61M 21/02 |
| 2020/0082928 | A1 * | 3/2020 | Wu | G16H 70/20 |
| 2020/0090641 | A1 * | 3/2020 | Kim | G06F 16/90332 |
| 2020/0337650 | A1 * | 10/2020 | Calhoun | A61B 5/7267 |
| 2020/0381117 | A1 * | 12/2020 | Spenciner | A61B 5/165 |
| 2021/0027648 | A1 * | 1/2021 | Higgins | G06F 3/04847 |
| 2021/0043099 | A1 * | 2/2021 | Du | G06N 3/006 |
| 2021/0050113 | A1 * | 2/2021 | Harle | G16H 50/20 |
| 2021/0202065 | A1 * | 7/2021 | Cummins | G16H 20/70 |
| 2021/0217408 | A1 * | 7/2021 | Hakkani-Tur | G06N 3/02 |
| 2021/0345925 | A1 * | 11/2021 | Davis | A61B 5/7435 |
| 2021/0383926 | A1 * | 12/2021 | Reid | G16H 50/30 |
| 2022/0179888 | A1 * | 6/2022 | Wang | G06F 16/3329 |
| 2022/0319705 | A1 * | 10/2022 | Feuerstein | G16H 10/60 |
| 2022/0382995 | A1 * | 12/2022 | Lee | G10L 15/06 |

OTHER PUBLICATIONS

Zhao et Eskenazi, "Towards End-to-End Learning for Dialog State Tracking and Management using Deep Reinforcement Learning" Sep. 15, 2016, arXiv: 1606.02560v2, pp. 1-10. (Year: 2016).*
Mohammadi et al., "CLaC at CLPsych 2019: Fusion of Neural Features and Predicted Class Probabilities for Suicide Risk Assessment Based on Online Posts" Jun. 6, 2019, pp. 34-38. (Year: 2019).*
Matero et al., "Suicide Risk Assessment with Multi-level Dual-Context Language and BERT" Jun. 6, 2019, pp. 39-44. (Year: 2019).*
Bitew et al., "Predicting Suicide Risk from Online Postings in Reddit The UGent-IDLab submission to the CLPsych 2019 Shared Task A" Jun. 6, 2019, pp. 158-161. (Year: 2019).*
Boukil et al., "Deep Learning Algorithm for Suicide Sentiment Prediction" Feb. 6, 2019, pp. 261-272. (Year: 2019).*
Bhat et Goldman-Mellor, "Predicting Adolescent Suicide Attempts with Neural Networks" Dec. 1, 2017, arXiv: 1711.10057v2, pp. 1-8. (Year: 2017).*
Rajendran et al., "Learning End-to-End Goal-Oriented Dialog with Maximal User Task Success and Minimal Human Agent Use" Jul. 17, 2019, arXiv: 1907.07638v1, pp. 1-12. (Year: 2019).*
Zirikly et al., "CLPsych 2019 Shared Task: Predicting the Degree of Suicide Risk in Reddit Posts" Jun. 6, 2019, pp. 24-33. (Year: 2019).*
Amir et al., "Quantifying Mental Health from Social Media with Neural User Embeddings" Apr. 30, 2017, arXiv: 1705.00335v1, pp. 1-17. (Year: 2017).*
Coman et al., "An Incremental Turn-Taking Model for Task-Oriented Dialog Systems" Jul. 11, 2019, arXiv: 1905.11806v3, pp. 1-5. (Year: 2019).*
Lee et al., "SUMBT: Slot-Utterance Matching for Universal and Scalable Belief Tracking" Jul. 17, 2019, arXiv: 1907.07421v1, pp. 1-6. (Year: 2019).*
Du et al., "System and Methods for Achieving Long-Term Goals Using an Artificial Intelligence Based Personal Assistant" Aug. 7, 2019, U.S. Appl. No. 62/884,075. (Year: 2019).*
Spenciner et al., "Dynamic Adaptation of Clinical Procedures and Device Assessment Generation based on Determined Emotional State" May 29, 2019, U.S. Appl. No. 62/854,179. (Year: 2019).*
Fadhil et al., "Assistive Conversational Agent for Health Coaching: A Validation Study" May 22, 2019, pp. 1-21. (Year: 2019).*
Inkster et al., "An Empathy-Driven, Conversational Artificial Intelligence Agent (Wysa) for Digital Mental Well-Being: Real-World Data Evaluation Mixed-Methods Study" 2018, pp. 1-14. (Year: 2018).*
Lubis et al., "Positive Emotion Elicitation in Chat-Based Dialogue Systems" Apr. 2019, pp. 866-877. (Year: 2019).*
Ghandeharioun et al., "Towards Understanding Emotional Intelligence for Behavior Change Chatbots" Jul. 23, 2019, pp. 1-7. (Year: 2019).*
Ilievski, Vladimir, "Building Advanced Dialogue Managers for Goal-Oriented Dialogue Systems" 2018, pp. 1-57. (Year: 2018).*
Cheong et al., "An intelligent platform with automatic assessment and engagement features for active online discussions" Jul. 2019, pp. 1-15. (Year: 2019).*
Gaur et al., "'Let Me Tell You About Your Mental Health!' Contextualized Classification of Reddit Posts to DSM-5 for Web-based Intervention" Oct. 2018, pp. 1-11. (Year: 2018).*
Chen et al., "Similar Minds Post Alike: Assessment of Suicide Risk by Hybrid Language and Behavioral Model" Jun. 2019, pp. 152-157. (Year: 2019).*

(56) References Cited

OTHER PUBLICATIONS

Ji et al., "Decentralized Learning with Average Difference Aggregation for Proactive Online Social Care" May 19, 2019, arXiv: 1905.07665v1, pp. 1-14. (Year: 2019).*
Kumar et al., "Anxious Depression Prediction in Real-time Social Data" Mar. 25, 2019, arXiv: 1903.10222v1, pp. 1-7. (Year: 2019).*
Ruiz et al., "CLPsych2019 Shared Task: Predicting Users' Suicide Risk Levels from Their Reddit Posts on Multiple Forums" Jun. 6, 2019, pp. 162-166. (Year: 2019).*
Hakkani-Tur et al., "Dialogue Systems" Sep. 6, 2018, U.S. Appl. No. 62/727,833, pp. i-54. (Year: 2018).*
Gaur et al., "Knowledge-aware Assessment of Severity of Suicide Risk for Early Intervention" May 2019, pp. 514-525. (Year: 2019).*
Zhong et al., "E3: Entailment-driven Extracting and Editing for Conversational Machine Reading" Jun. 12, 2019, arXiv: 1906.05373v1 , pp. 1-11. (Year: 2019).*
Budzianowski et Vulic, "Hello, It's GPT-2—How can I Help You? Towards the Use of Pretrained Language Models for Task-Oriented Dialogue Systems" Aug. 4, 2019, arXiv 1907.0577v2, pp. 1-8. (Year: 2019).*
Howard et al., "Transfer Learning for Risk Classification of Social Media Posts: Model Evaluation Study" Jul. 10, 2019, arXiv: 1907.02581v2, pp. 1-18. (Year: 2019).*
Chao et Lane, "BERT-DST: Scalable End-to-End Dialogue State Tracking with Bidirectional Encoder Representations from Transformer" Jul. 5, 2019, arXiv: 1907.03040v1, pp. 1-5. (Year: 2019).*
Conway et al., "Time Masking: Leveraging Temporal Information in Spoken Dialogue Systems" Jul. 25, 2019, arXiv: 1907.11315v1, pp. 1-6. (Year: 2019).*
Gotz, David, et al., "Visual Cluster Analysis in Support of Clinical Decision Intelligence," AMIA Annual Symposium Proceedings, 2011 pp. 481-490.
Cover Sheet indicating date for Gotz, David, et al., "Visual Cluster Analysis in Support of Clinical Decision Intelligence," AMIA Annual Symposium Proceedings, 2011 pp. 481-490.

* cited by examiner

ASSISTANCE IN RESPONSE TO PREDICTIONS IN CHANGES OF PSYCHOLOGICAL STATE

CLAIM OF PRIORITY

This application claims priority under 35 USC § 119(e) to U.S. Provisional Patent Application Ser. No. 62/886,519, filed on Aug. 14, 2019, and entitled "ASSISTANCE IN RESPONSE TO PREDICTIONS IN CHANGES OF PSYCHOLOGICAL STATE," the entire contents of which are hereby incorporated by reference.

BACKGROUND

This disclosure relates to assistance triggers to detect changes in a user's status.

Data is available in many forms for many topics and from many sources. The Internet is one example of a data source. The Internet has become an important tool to conduct commerce and gather information. Other sources of data include notes taken on observations including observations of patients that are seeking mental health services. One particularly affected population of individuals, some of which seek mental health services, are current or former members of armed services, i.e., military personal.

The Durkheim Project was a real-time analysis of the psychological health of returning veterans, and the prediction of negative events such as suicide. The project used data in analyzing the social and mobile interactions of thousands of veterans to more accurately predict suicide. One such predictive effort is described in U.S. Pat. No. 9,817,949, entitled: "Text Based Prediction of Psychological Cohorts," the contents of which are incorporated herein by reference.

SUMMARY

Described are processes including methods, computer program products and apparatus that use a mental state classifier, such as a suicidality classifier that interfaces with a mobile application for providing intervention brokering and peer-to-peer resource allocation to individuals at risk. The areas of risk include, but are not limited to: mental health (e.g. suicidality), addiction (e.g. drugs), weight loss, and financial distress (e.g. potential homelessness).

According to an aspect, a computer implemented process includes receiving user set goal, querying a database to determine whether there is a machine learning model that predicts a risk associated with the received goal, receiving results of execution of the machine learning model, assessing changes in a real-time risk value associated with the received goal, generating a dialog associated with assessed changes in the real-time risk value associated with the goal, posting to a buddy system, the real time risk value with the generated dialog, and tracking edits made on the buddy system.

The above aspect may include amongst features described herein one or more of the following features.

The machine learning model is one or more of a mental health model, a suicidality classifier model, a suicide ideation classifier model, a losing weight model, or a saving money model. The model is one or more of mental health model, a suicidality classifier model, a suicide ideation classifier model. When the system does not have a model, the method further includes generating by the system a machine learning model that predicts a risk associated with the received goal. When the system does have a model, the method further includes generating by the system a machine learning model that predicts a risk associated with the received goal.

The method further includes generating the dialogue correlated to wording appropriate to the risk and sending the generated dialog to the buddy system. The method further includes receiving edits to the generated dialog and tracking the received edits to the generated dialog. Tracking further includes adapting suggested text in a future generated dialog based on a count of edits.

According to an additional aspect, a computer program product tangibly stored on a non-transitory computer readable storage device includes instructions for causing a processor to receive user set goal, query a database to determine whether there is a machine learning model that predicts a risk associated with the received goal, receive results of execution of the machine learning model, assess changes in a real-time risk value associated with the received goal, generate a dialog associated with assessed changes in the real-time risk value associated with the goal, post to a buddy system, the real time risk value with the generated dialog, and track edits made on the buddy system.

The above aspect may include amongst features described herein one or more of the following features.

The product further includes instructions to generate the dialogue correlated to wording appropriate to the risk and send the generated dialog to the buddy system. The product further includes instructions to receive edits to the generated dialog and track the received edits to the generated dialog. The product further includes instructions to adapt the suggested text in a future generated dialog based on a count of edits.

According to an additional aspect, an apparatus includes a processor, a memory coupled to the processor, and a computer readable storage device storing a computer program product for mental state classification, the computer program product comprises instructions for causing the processor to receive user set goal, query a database to determine whether there is a machine learning model that predicts a risk associated with the received goal, receive results of execution of the machine learning model, assess changes in a real-time risk value associated with the received goal, generate a dialog associated with assessed changes in the real-time risk value associated with the goal, post to a buddy system, the real time risk value with the generated dialog, and track edits made on the buddy system.

The above aspect may include amongst features described herein one or more of the following features.

The apparatus further includes instructions to generate the dialogue correlated to wording appropriate to the risk and send the generated dialog to the buddy system. The apparatus further includes instructions to receive edits to the generated dialog, and track the received edits to the generated dialog. The apparatus further includes instructions to adapt the suggested text in a future generated dialog based on a count of edits.

One or more of the following advantages may be provided by one or more of the above aspects.

A new type of App is disclosed for the purposes of determining goal-setting individuals such as veterans at risk, intervention brokering, and peer to peer resource allocation. The areas of risk include, but are not limited to, mental health (e.g. suicidality), addiction (e.g. opioids), weight loss, and financial distress, potential homelessness, and so forth.

The App can be scaled to meet the needs of goal setters, e. g., veterans in treatments to mental health, opioid addiction, and the financial risks, or for any other goal setter that establishes goals but needs reinforcement to maintain and achieve set goals. The App provides end-to-end opt-in tracking and resource allocation that can fundamentally provide a high degree of personal attention and speed and can be important in addressing needs in rural communities, served by the Internet, but not clinical services.

DESCRIPTION

Figure 1:
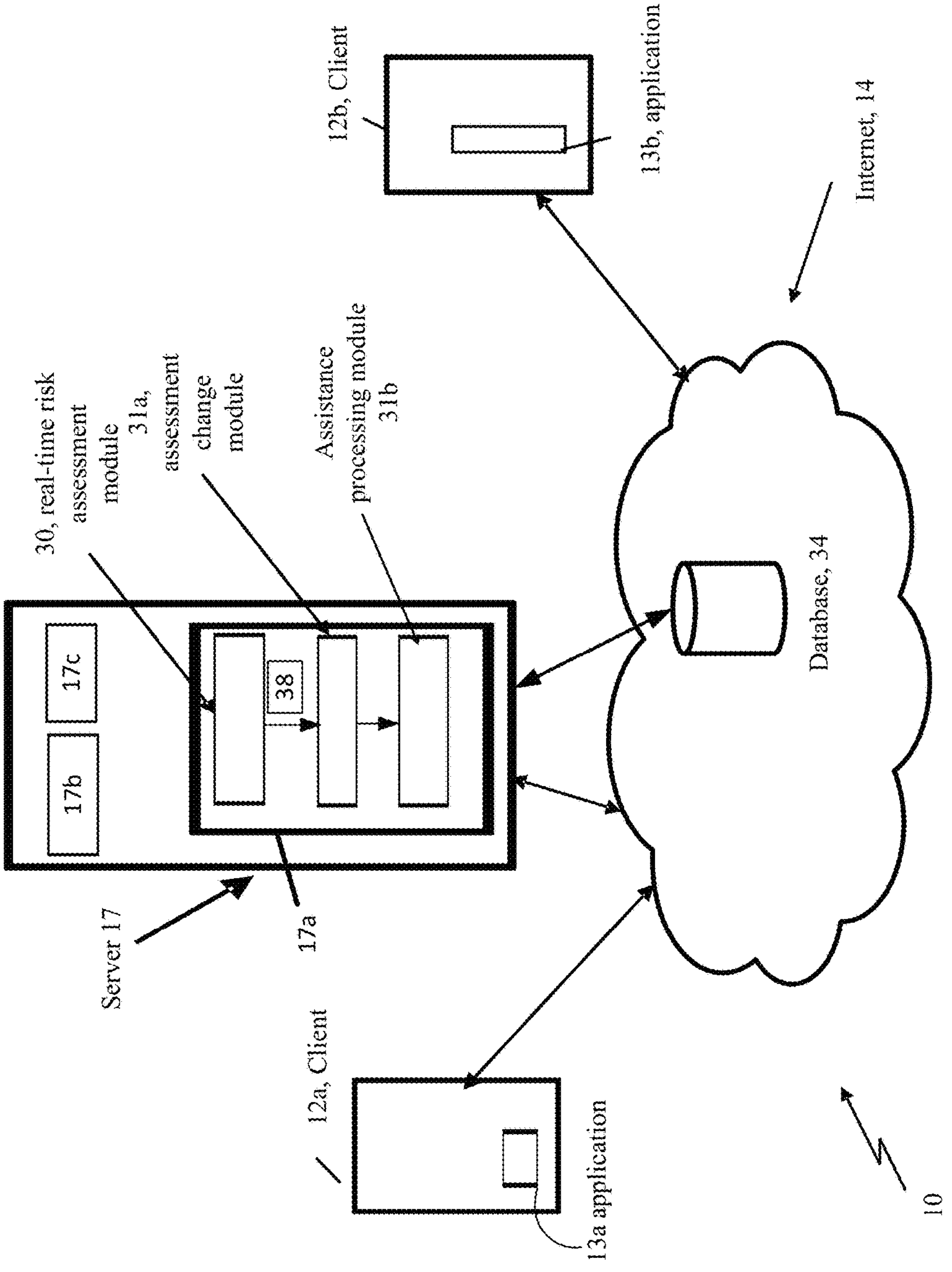
FIG. 1 is a block diagram of system employing assistance triggered by data analysis software.

Referring to FIG. 1, a networked computer system 10 includes client devices 12*a*-12*b* executing client apps 13*a*, 13*b* connected to a server system 17 through a first network, e.g., the Internet 14, such as the cloud, or a private network. The client devices 12*a*-12*b* run the application programs 13*a*-13*b* that receive data from the server computer 17. Server computer 17 executes a real-time risk assessment 30, such as an ideation classifier, as discussed in the above incorporated by reference patent, and that resides on a computer readable medium 17*a*, e.g., disk or in memory for execution. In addition to the real-time risk assessment 30, as discussed in the above incorporated by reference patent, the system 10 also includes assessment change module 31*a* that analyzes predictions generated by the real-time risk assessment module 30 and trigger assistance processing module 31*b*.

Generally speaking, the real-time risk assessment 30 analyzes data obtained from, e.g., records of patients seeking medical attention, as discussed in the above incorporated by reference patent. The risk assessment module 30 produces from that data one or more risk assessments for one or more individuals. Some of the details of the real-time risk assessment 30 are discussed below, but the reader is invited to refer to the incorporated by reference patent for further details on the risk assessment 30 module.

The risk assessment module provides input to the assessment change module 31*a*. The assessment change module 31*a* stores and tracks assessments made by the real-time risk assessment 30 that can trigger assistance processing module 31*b*. Although the real-time risk assessment 30 and the assessment change module 31*a* are shown in FIG. 1 residing on a server 17 that can be operated by an intermediary service, the real-time risk assessment 30 and the assessment change module 31*a* could be implemented as a server process on a client system 12 or as a server process on a corporate or organization-based server.

On the server 17, the real-time risk assessment 30, the assessment change module 31*a* and the assistance processing module 31*b* each include analysis objects that are persistent programming objects, i.e., stored on a computer hard drive 17*a* of the server in a database 34. At invocation of the real-time risk assessment 30 and the assessment change module 31*a*, the analysis objects are instantiated, i.e., initialized with parameters by a processor device (e.g., central processing unit) 17*b* and placed into main memory 17*c* of the server 17, where they are executed.

As described in the above Issued Patent, the output from the risk assessment module 30 is a result object 38 in the form of a prediction table that can be output as an HTML or equivalent web page. The result object 38 will include information as to a database or text representation of relationships between parent and child data. Formats for the data can be ".net" files (industry standard file format for a feature vector). Alternatively, other formats can be used such as a standard text file and so forth.

The results object 38 is input to the assessment change module 31*a*. The assessment change module 31*a* compares current status of an individual to a prior status pattern(s) and if there is a change in current status and the change is a prediction of an elevation in risk behavior, the assessment change module 31*a* triggers invocation of the assistance processing module 31*b*. At invocation of the assistance processing module 31*b*, the analysis objects are instantiated, i.e., initialized with parameters and placed into main memory 17*c* of the server 17, where they are executed.

A process for configuring the real-time risk assessment 30 can be as described in the Issued Patent (or if a different risk assessment process is provided it would be configured accordingly.)

Figure 2:
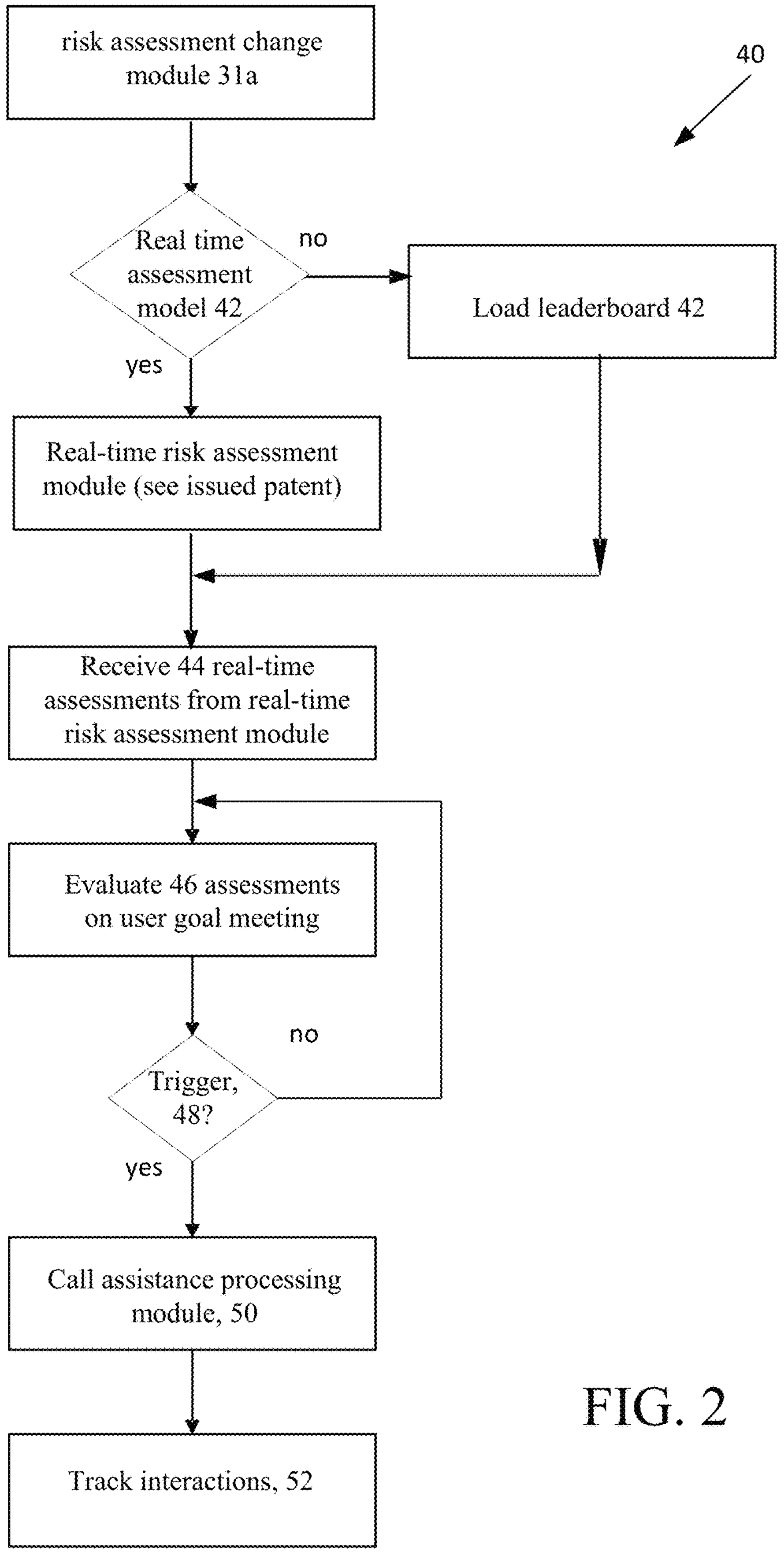
FIG. 2 is a flow chart showing data analysis for triggering assistance.

Referring to FIG. 2, a process 40 for operating the assessment change module 31*a* involves ranking users against a model or if not available, against a cohort (leaderboard) of relative risk. The process loads the leaderboard, receives real-time assessments and evaluates how well the user is meeting the goals (both set and assumed goals). Specifically, users are ranked against goals they have overtly committed to (e.g. "Be Mentally Healthy"), and any assumed goals (e.g. "suicide risk"). The assessment change module 31*a* is an artificial intelligence (AI) app that executes on server 17 and is used for goal setting and determining deviations from the set goals.

In the system 10 there are two basic roles that users may have one role is "a goal setter" that uses client device 12*a* and the other role is "a buddy" that uses client device 12*b*. The goal setter's client device 12*a* could be similar to the buddy client device 12*b*, but being loaded with a different version/portion of the App.

Goal setters are people who specify goals, while buddies are individuals that help goal setters achieve their goals through positive text reinforcement. (Note in practice users can act in both roles, e.g., a goal setter could be paired with a buddy, and yet could be a buddy for his buddy that sets his own goals or could be a buddy for a different goal setter.) The relative rank of the goal setter user (per risk) is provided by the real-time risk assessment 30.

The assessment change module 31*a* tracks both "overt" goals (e.g., goal-setter set goals, such as positive mental health), and "assumed" goals, such as avoiding risk for suicide. Specifically, "overt" goal setting provides engagement and gamification (discussed below), while "assumed" goals protect the user from epidemiological risks, detected at a large population level (e.g. suicidality).

Figure 3:
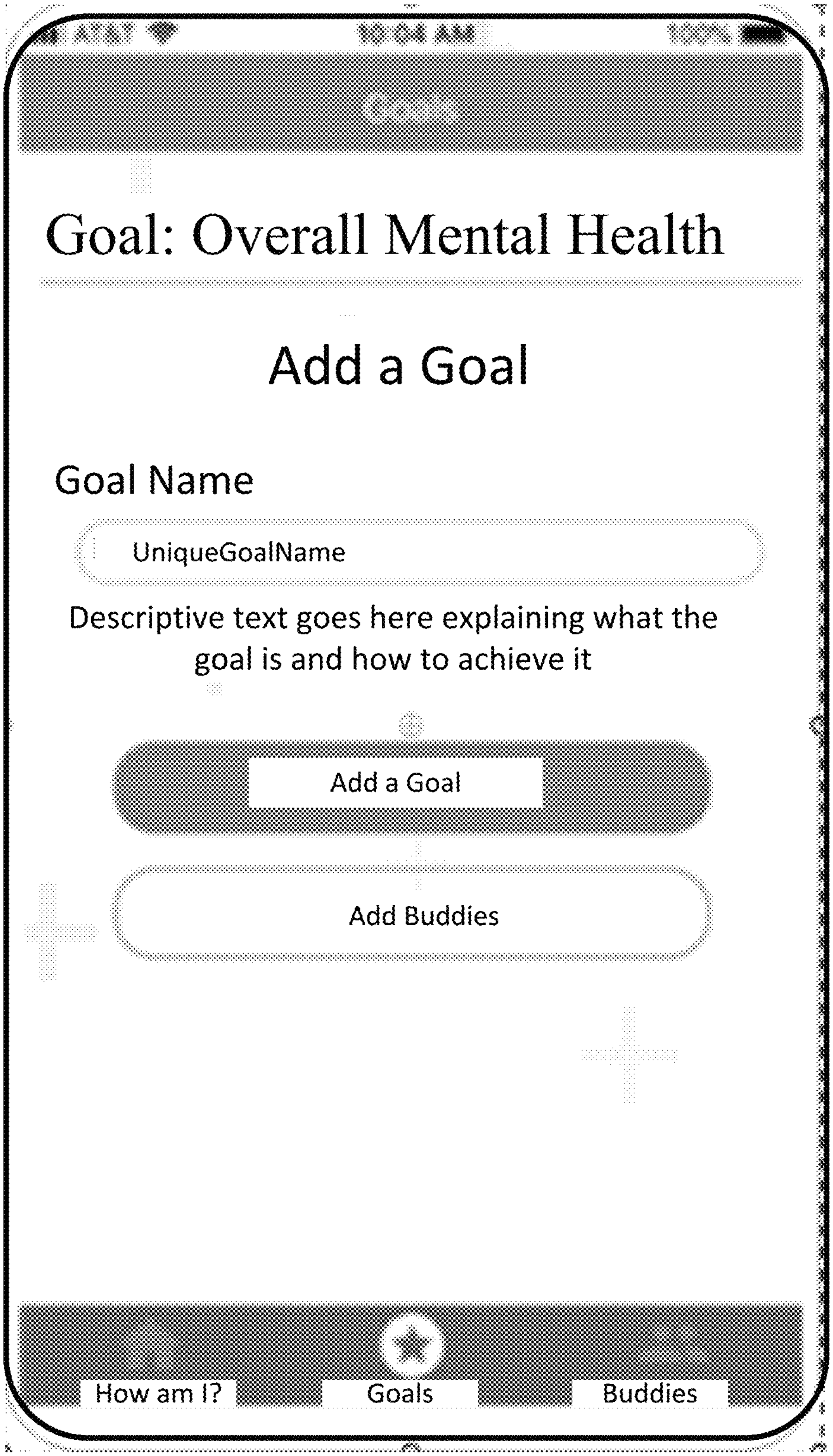
FIG. 3 is a diagram depicting a portable device, e.g., smartphone with a user interface for producing/adding a goal.

Configuring the assessment change module 31*a* can be accomplished in the app through one or more user interface screens, such as depicted in FIG. 3, which is used by the goal setting user for goal setting and adding buddies. Goal setting involves a descriptive text explaining the goal and how to achieve the goal. Adding buddies involves adding a user name, contact information, e.g., telephone no. or other mechanism by which the assistance processing module 31*b* can contact the buddy's client device 12*b*.

In operation, the assessment change module 31*a* determines existence of a model 42 or a leaderboard, and if the model exists receives 44 the updates on evaluated assessments from the real-time risk assessment module 30 of a goal setter user's goal accomplishments. Otherwise, the assessment change model 31*a* loads a leaderboard that acts as a proxy for the model. The assessment change module 31*a* evaluates 46 the updated assessments from the real-time risk assessment module 30 and forms a current assessment. If the current assessment represents a signification change, e.g., a negative change (indicating deterioration in user meeting set or implied goals), the assessment module 31*a* triggers 48 the assistance processing module 31*b* to call in assistance 50 to the goal setter user's "buddy" (or buddies) client device(s) 12*b*. The assessment module 31*a* having triggered the assistance processing module 31*b* to call for assistance of the goal setter user's "buddy," (or buddies) client device 12*b* tracks 52 interactions between the goal setter and the "buddy" or buddies.

An exemplary Goals UI questionnaire could be as follows:

If I want to . . .

Look to be [e.g. "be mentally healthy"]//[Looking_For] is a system value

Avoiding [e.g. "bad habits"]//[Avoiding] is a system value Suggested goals:

Available goals (ranked/presented based on popularity, we will start with "Be Mentally Healthy")

. . . Then I am able to set a new goal.

Figure 4:
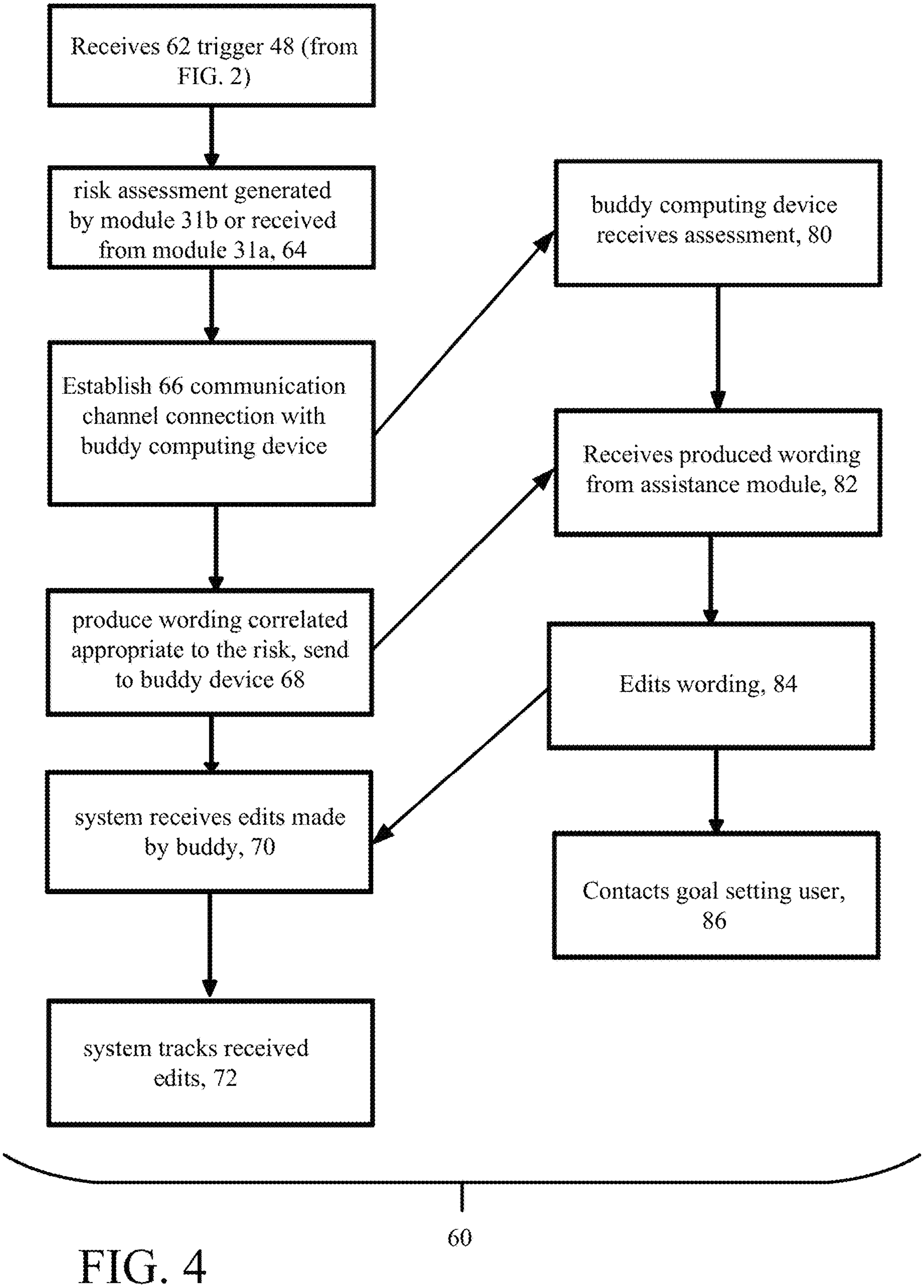
FIG. 4 is a flow chart depicting assistance interaction.
Figure 5:
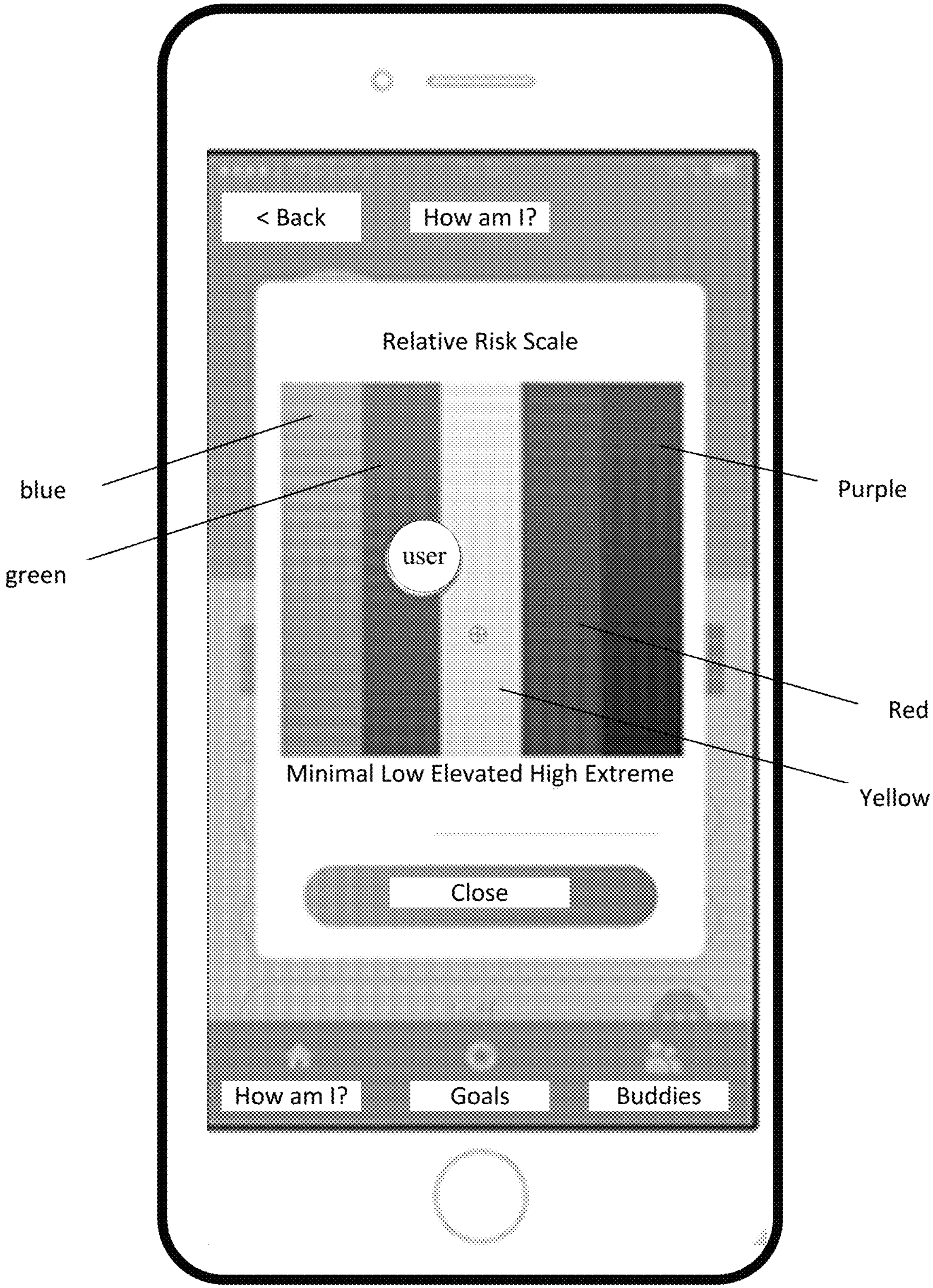
FIG. 5 is a diagram depicting a portable device, e.g., smartphone, with a user interface for rendering a risk score associated with meeting a goal.

Referring now to FIG. 4, processing 60 perform by the assistance processing module 31*b* and the buddy device 12*b* are shown. The assistance processing module 31*b* receives the trigger 48 (FIG. 2) from the assessment change module 31*a* that evaluated the received assessment updates from the real-time risk assessment module 30 for a given goal setter user. Either the assessment change module 31*a* generates 64 or causes the assistance processing module 31*b* to generate a risk assessment that can be sent to the user's buddy (or buddies) device(s) 12*b* and optionally to the goal setting user. (An exemplary risk assessment is depicted in FIG. 5, and discussed below).

The assistance processing module 31*b* establishes a communication channel connection with the buddy client device 12*b*, e.g., a cell phone or smart phone, or other devices 66, and sends to the buddy client device 12*b*, a dialogue that has wording correlated approximately appropriate to the risk 68. For example, blue might be extremely low risk, and therefore, click positive reinforcement "good going," whereas red would be higher risk relative to blue, and the buddy would be prompted to try to solve the risk that was assessed.

The buddy client device 12*b* generally edits the received dialogue. The assistance processing module 31*b* receives the edits 70 from the buddy client device 12*b* (see below). The buddy client device 12*b* sends the edited text to the user client device 12*a* to provide a more realistic "human to human" type of contact with the goal setting user. The system 10 tracks the edited entries 72 sent to the user device 12*a*.

As part of the tracking, the system 10 adapts the suggested text in future trigger episodes, for example, based on counts of edits. Upon being triggered by the assistance processing module 31*b*, the buddy can either call or text the goal setting user client device 12*a* and use text scripts that were edited by the buddy based on text scripts produced by the assistance processing module 31*b*.

The buddy computing device receives 80 the assessment from the risk assessment module 30, and receives 82 the produced wording from the risk assessment module 31*b*. The buddy client device 12*b* using an editor program edits 84 the received text to fit the recipient. The buddy client device 12*b* sends the edits to the assistance processing module 31*b* and contacts the goal setting user device 12*a*. For example, the buddy client device 2*b* sends the edited text to the user client device 12*a* to provide a more realistic type of "human to human" contact with the goal setting user or can use the edited text to converse with the user during a call made to the goal setting user device 12*a*. The assistance processing module 31*b* can also monitor interactions between the buddy client device 12*b* and the goal setter user client device 12*a*.

Referring to FIG. 5, a risk assessment interface 90 is shown render on the buddy client device 12*b*. Risk assessment is generated for each goal setting user. For instance, positive or negative mental health scores are displayed. For each goal in the database 34, the database 34 is queried (via Rest procedure call) for a given user and risk model. All goal entries (i.e., typed in by users) are stored in the database 34, as candidates for future risk model generation. As shown in FIG. 5, a chart can be displayed on the buddy client device 12*b* and the chart can be color coded from blue to green to yellow to red to purple, denoting successively increasing risk levels. The risk assessment interface renders an indicium 92 indicating where on the risk assessment chart the particular goal setting user is rated. This interface can also be displayed on the user device 12*a*, as shown in FIG. 5.

Goal setting users can be segmented into 5 color code quintiles (or segments): Blue, Green, Yellow, Red, Purple)

1. Blue Dialog: "Hey [USER], you're doing great. Keep up the good work on [OVERT_GOAL], and you will be the best!"
2. Green Dialog: "Hey [USER], your almost there on [OVERT_GOAL], keep at it!"
3. Yellow Dialog: "Hey [USER], seems like you need some help with [OVERT_GOAL], can I help?"
4. Red Dialog: "Hey [USER], are you ok with regards to [OVERT_GOAL]?"
5. Purple Dialog: "Hey [USER], let's talk about [OVERT_GOAL] soon. Seems like it's not going well."

The variables isolated are [USER], [OVERT_GOAL], and a hidden variation [RANK].

Figure 6:
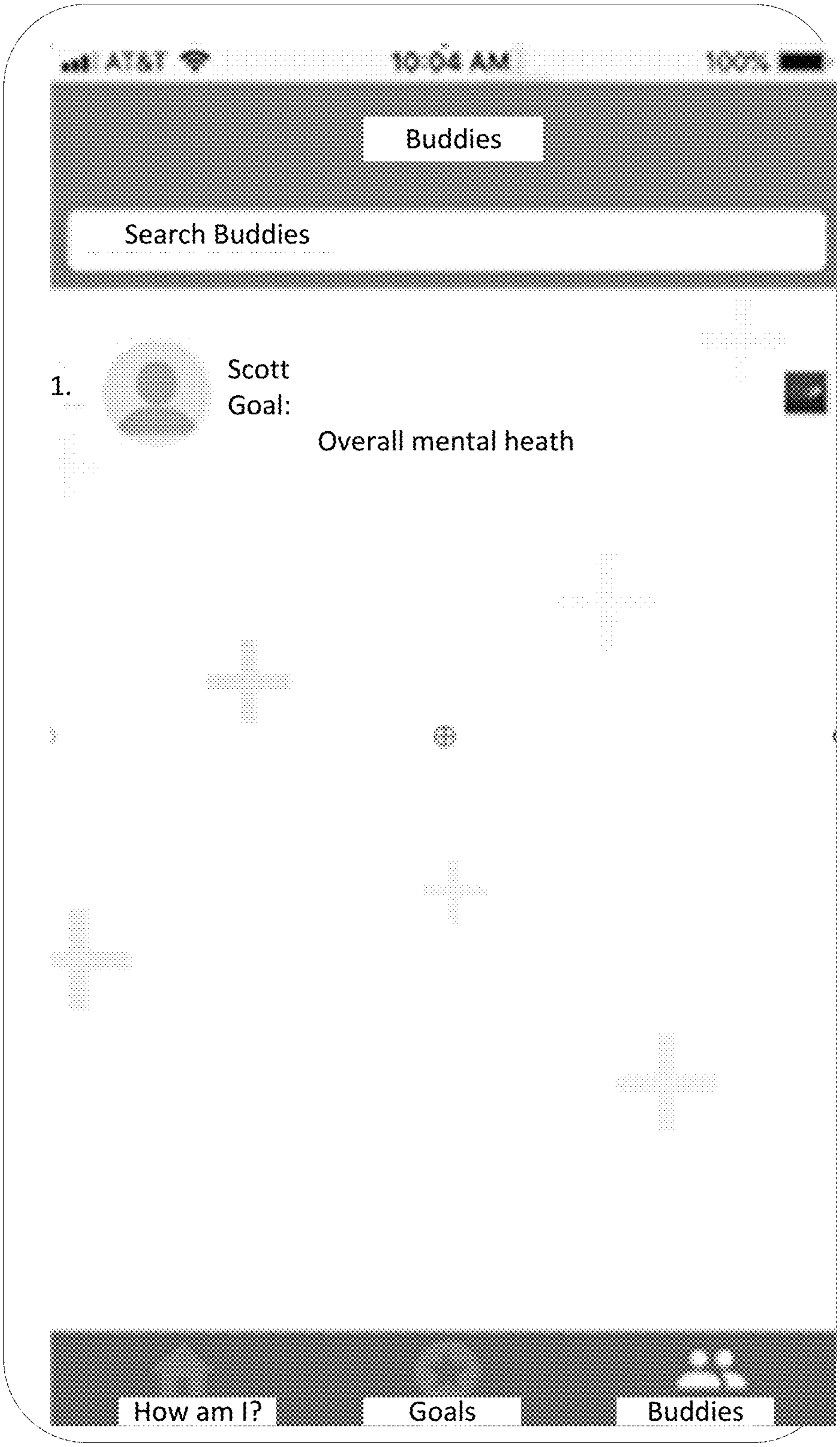
FIG. 6 is a diagram depicting a portable device, e.g., smartphone, with a user interface for rendering assistance to a goal setter.

Referring to FIG. 6, a buddy-user chat session is shown. FIG. 6 shows the buddy client device 12*b* of a buddy, e.g., a smartphone, with the user interface for rendering assistance to the goal setting user. When the buddy chats with the goal setting user, system recommended dialogue appears, in-line with the risk. For each goal, several, e.g., five different messages may be generated for the buddy, as suggested messages to convey to the goal setter user.

An exemplary implementation can be a cross platform XAML application running Xamarin™ on the Microsoft Azure cloud 14 for production. (Other processing environments could be used.) The app displays multiple custom user interface screens (one search window, & one gamified leaderboard (see below). User to user communication is through in-app SMS (simple messaging service), though the system could support system generated emails. The app's database 34 can resides on the Internet 14, e.g., in the Azure cloud. The app supports a simple dashboard for controlling editing of the specific positive reinforcement messages, etc. The App could be configured for being downloaded from an app store.

A workflow is as follows: a user defines a goal, a model is retrieved/generated, goal progress is evaluated by an AI engine, e.g. assessment change module 31*a*, suggestions are generated by an AI engine, e.g., assistance processing module 31*b* and sent to a buddy client device 12*b* that can edit the suggestions and sends the edited suggestions to the user client device 12*a*. The real-time risk assessment 30 can include the assessment change module 31*a* and the assistance processing module 31*b* or these can be separate modules.

The real-time risk assessment 30 is built from ontology-based data, as discussed in the Issued Patent. In the real-time risk assessment 30 preprocessing of the data is performed. A database containing text strings from various sources is selected. The text strings represent any alphanumeric text data and in particular represent records of patients seeking medical attention. The database of the text strings need not be in any particular structure. The process takes the text data from the database and filters noise from the data, such as HTML tags and scripts, extra spaces, extra or inaccurate punctuation and irregular characters. In addition, noise can be somewhat problem specific, as is discussed below.

A leaderboard is depicted below, (three colors may be identified, green, yellow and red, (not shown) to signal changes).

Simple Leaderboard

| | Score | Goal 1 Rank | Rank Diff |
|---|---|---|---|
| User 1 | 667 | 1 | 1 |
| User 2 | 548 | 2 | 0 |
| User 3 | 222 | 3 | −1 |

The leaderboard has columns for name, score (percentage or points) Goal rank(s) one goal rank shown and rank difference, as determined for specific goal(s).

For the goal setter view, the leaderboard chart should:

Be per an overt goal

Be anonymous (in presentation layer)

Allow the switching of goals (at the bottom)

For the buddy view, the leaderboard chart should:

Display the goal setter's leaderboard (can side scroll other leaderboards, if multiple.)

Suggest text intervention

*Leaders could be displayed as Alphas "α", and the absolute lowest Omegas "ω"?

Chat feedback:

ability to easily modify these messages for the goals (e.g., simple research dashboard)

The buddy can type custom messages, and has the ability to set as automated/repeated reminders. (e.g. "Hey man, remember that I have your back, John.) Custom messages should be stored in database 34 or in a separate/dedicated database (not shown).

As discussed in the Issued Patent, the data are selected to provide a dataset that will be used to structure the data into child variables for analysis. The process builds a parent and child relationship model from the dataset. The parent/child relationship model is defined as the parent variable being the desired outcome, e.g., how often would the process expects to obtain a result, e.g., of parent possibilities. The child relationships are the prior knowledge that the risk assessment module 30 examines to determine the parent possibilities. The process determines what text data are relevant to the inquiry and the text data that needs to be examined by the process, given a known structure of text data, the state of probability is the prior knowledge, i.e., how many text data have been used out of that structure. The process chooses the actual variables to examine by choosing the child variables, e.g., the prior data for inclusion in a dataset.

Conditional probabilities are used to build the classifier's model and the eventual ontology. That is, relationships are determined for multiple child variables to the parent variable. Thus, while determining probabilities values uses conditional probabilities, basic probabilities (e.g., child to parent child to parent serial type of analysis) could also be used. Multiple routines determine conditional probability by measuring condition probability of each child variable based on the relevance of each child variable to the parent variable. The determined conditional probabilities are aggregated and compare aggregated conditional probabilities to parent.

A filter is employed to remove context specific noise, e.g., data that are not relevant to the inquiry from the dataset, and the process defines the parent variable, and builds the statistical model from the dataset and parent variable. A statistical engine, algorithm or filter (hereinafter engine) defines the parent relationships between the child variables in the child variable dataset and the parent variable. The process determines incidence values for each of the child variables in the dataset. The incident values are concatenated to the data strings to provide the child variables. The child variables are stored in a child variable dataset.

One example of a statistical engine is a Bayesian Statistical engine to define correlative relationships. Others could be used such as a genetic algorithm as discussed below or other type of statistical classifier language. A statistical engine defines correlative relationships between child and parent variables. Other more complex relationships can be defined such as child to child relationships. The engine processes the dataset to produce child and parent variables that are defined by applying the engine to the dataset to establish relationships between the child and parent variables.

The reader is referred to the above Issued Patent for further details. A specific example of workflow preprocessing applying to finance is further set out in the issued U.S. Pat. No. 7,516,050 "Defining the Semantics of Data Through Observation," the contents of which are incorporated herein by reference. The features of that patent can be adapted to provide a workflow process for risk assessment.

Figure 7:
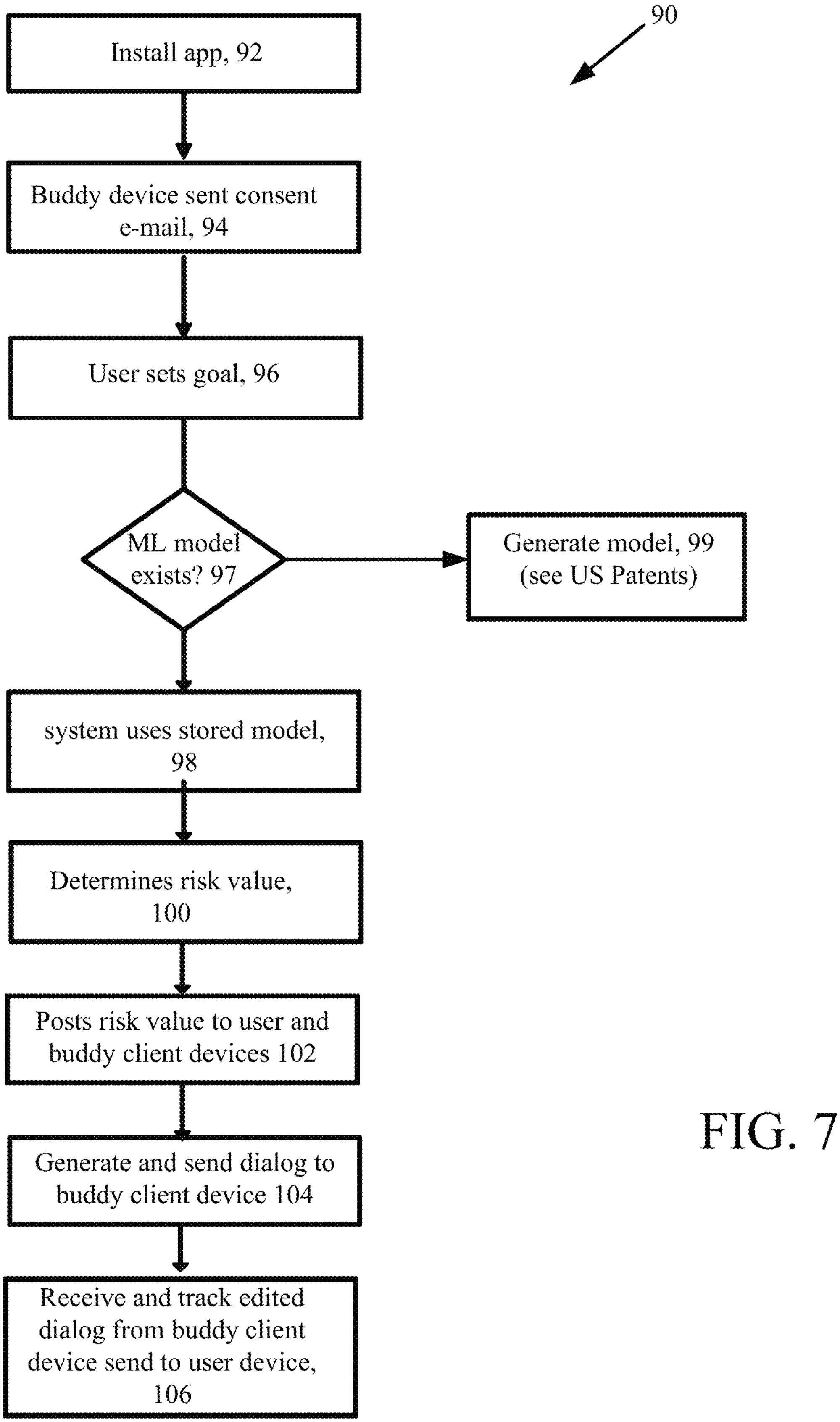
FIG. 7 is a flow chart depicting an general example.

Referring now to FIG. 7, a generalized process 90 can now be described. The App is installed with password and/or registered with password 92. A registration Page can include a goal setters name, email or phone number, buddy name, buddy email or phone number. The goal setting user can be redirected to an Opt-In consent form (HTML). The buddy receives 94 an email or SMS with consent app download link.

A user sets a goal 96. While the goal as discussed above was describe in terms of mental health (suicide) and which required the use of and/or generation of a suicidality classifier, e.g., a suicide ideation classifier based on the text contained within a set of records, the goal can be any goal, such a losing weight or saving money, etc.

Upon entering the goal the system queries the system database 34 to determine 97 whether the system database 34 has a machine learning model to predict risk associated with the goal. If the system has a machine learning model, the system uses 98 the stored ML model to assess risk. If the system does not have a machine learning model, the system generates 99 a model automatically. Initially the model may not have a high level of predictive accuracy at first, but over time is trained and predictive accuracy will improve.

Presume the existence of an appropriate model, e. g., a suicidality classifier that will be the analysis topic for this discussion. The assessment change module 31*a* determines 100 real-time risk value that is posted both to the user client device 12*a* as a color-coded chart, and to the buddy client device 12*b* with a dialog. The assistance processing module generates 104 the dialogue correlated to wording appropriate to the risk, and sends the dialog to the buddy system on which the dialog is edited in a manner that fits the intended recipient, i.e., the goal setting user, as discussed above. The assistance processing module 31*b* receives and tracks 106 edits received from the buddy client device 12*b* and sends the edited text to the user client device 12*a*, as discussed above. The assistance processing module 31*b* can adapt its suggested text in future based on counts of edits, with edits having a high frequency number of edits being given more prominence in modifying suggested text than counts of lower frequency values.

Other models can be used. For example, a suicide ideation classifier based on the text contained within a set of records, a weight loss model or a money saving money, etc.

Figure 8:
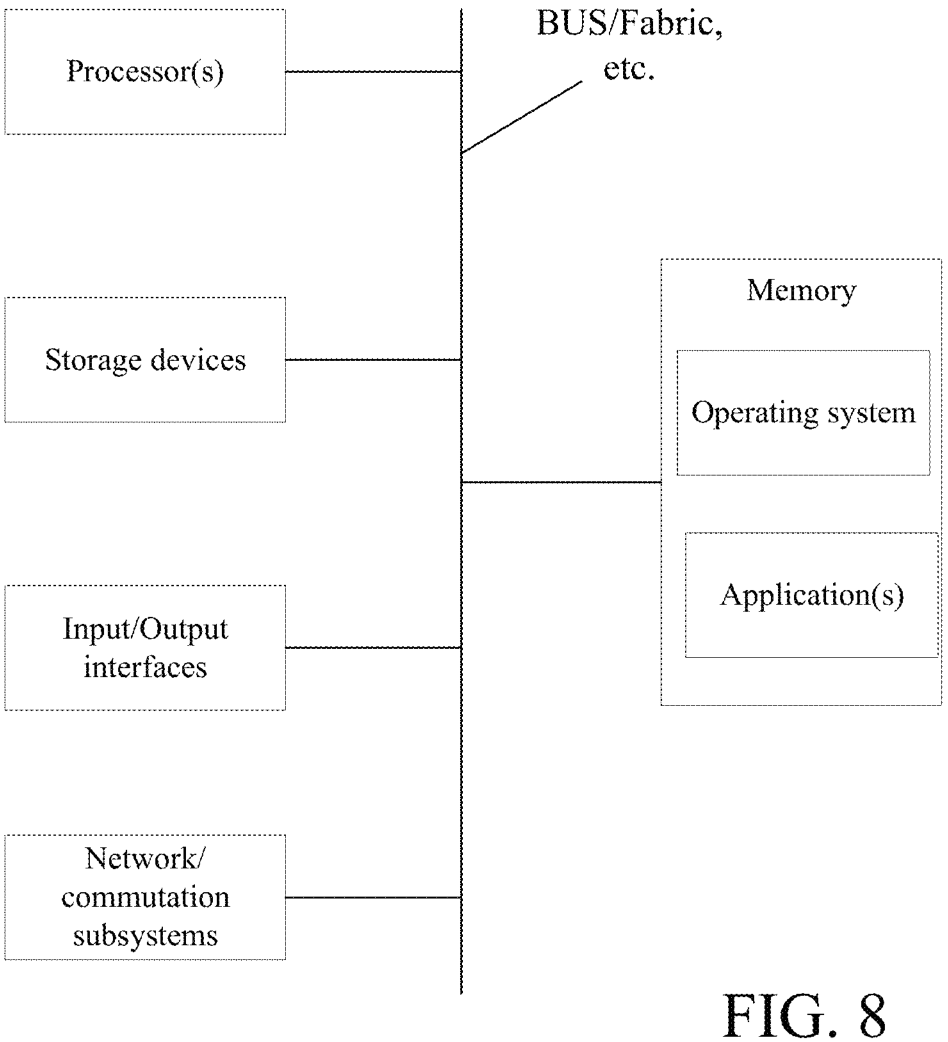
FIG. 8 is a block diagram of a computer system and/or computer device.

Referring now to FIG. 8, the essential elements of a computer system or device are a processor(s) for performing actions in accordance with instructions and one or more memory devices for storing instructions and data. Generally, a computer will also include, or be operatively coupled to I/O interfaces, network/communication subsystems, and one or more mass storage devices for storing data (e.g., magnetic, magneto optical disks, or optical disks).

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A computer-implemented method comprising:

configuring, by one or more networked computer systems, an assessment change module by:

causing rendering on a first client device of one or more user interface screens with a portion for entering text specifying a goal and another portion for specifying contact information of a buddy system, with the first client device being associated with a user;

executing the assessment change module, comprising instantiating analysis objects that are persistent programming objects stored in a database on a computer hard drive of a server by:

initializing parameters by a processor; and placing the analysis objects with initialized parameters into memory, where they are executed;

receiving, through one or more of the rendered user interface screens of the assessment change module from the first client device over a network, a user-set goal that is specified by the user of the first client device;

querying a database storing a plurality of machine learning models that each predict a psychological risk value to determine whether one of the plurality of machine learning models predicts a psychological risk value associated with the user-set goal specified by the user of the first client device and received through the portion of the one or more of the user interface screens for entering text specifying the goal;

in response to determining that one of the plurality of machine learning models predicts the psychological risk value associated with the received goal, obtaining two or more psychological risk values outputted by that machine learning model;

causing rendering on a second client device of a risk assessment interface generated for the user, wherein the risk assessment interface comprises a color coded risk assessment chart with a plurality of colors denoting successively increasing risk levels, and wherein the risk assessment interface renders an indicium indicating where on the risk assessment chart the user having specified the user-set goal is rated;

assessing, by the assessment change module based on the two or more outputted psychological risk values, temporal changes in a real-time psychological risk value associated with the user-set goal specified by the user of the first client device and received through the portion of the one or more of the user interface screens for entering text specifying the goal;

based on contact information specified in the portion of the one or more user interface screens, generating by one or more networked computer systems a dialog between the first client device and the buddy system, with the dialog associated with the assessed temporal changes in the psychological real-time risk value associated with the goal;

executing an assistance processing module that comprises analysis objects that are persistent programming objects stored in a database on a computer hard drive of a server, comprising:
instantiating the analysis objects by initializing parameters and placing the analysis objects into memory of the server where they are executed;
posting by the assistance processing module to the buddy system, the generated dialog;
tracking by the assistance processing module edits to the generated dialog made on the buddy system; and
at a time subsequent to the tracking of the changes, outputting, by the assistance processing module to the buddy system, another generated dialog with suggested text based on past edits, with past edits having been made more frequently being given more prominence in modifying suggested text than past edits being made less frequently.

2. The computer-implemented method of claim 1, wherein the one or more user interface screens are:
one or more user interface screens of one or more HTML pages; or
one or more user interface screens of one or more web pages.

3. The computer-implemented method of claim 1 wherein the one of the plurality of machine learning models is one or more of a mental health model, a suicidality classifier model, or a suicide ideation classifier model.

4. The computer-implemented method of claim 1, wherein the method comprises generating a newly-generated machine learning model that predicts the psychological risk value associated with the received goal in response to determining there is no machine learning model in the plurality of machine learning models that predicts the psychological risk value associated with the received goal.

5. The computer-implemented method of claim 1, wherein the method comprises loading a leaderboard that is indicative of a psychological risk associated with the received goal in response to determining there is no machine learning model in the plurality of machine learning models that predicts the psychological risk value associated with the received goal.

6. The computer-implemented method of claim 1 wherein generating the dialog comprises:
generating the dialog correlated to wording appropriate to the assessed temporal changes in the psychological real-time risk value.

7. The computer-implemented method of claim 6, wherein posting to the buddy system comprises:
posting to the buddy system, the real-time psychological risk value.

8. The computer-implemented method of claim 7 wherein tracking the changes to the generated dialog made on the buddy system comprises tracking a count of changes made to the generated dialog, and wherein the method further comprises:
adapting a subsequent generated dialog based on the count of changes made to the generated dialog.

9. A computer program product tangibly stored on a non-transitory computer readable storage device, the computer program product comprising instructions for causing a system to:
configure an assessment change module by:
causing rendering on a first client device of one or more user interface screens with a portion for entering text specifying a goal and another portion for specifying contact information of a buddy system, with the first client device being associated with a user;
execute the assessment change module, comprising
instantiating analysis objects that are persistent programming objects stored in a database on a computer hard drive of a server by:
initializing parameters by a processor; and
placing the analysis objects with initialized parameters into memory, where they are executed;
receive, through one or more of the rendered user interface screens of the assessment change module from the first client device over a network, a user-set goal that is specified by the user of the first client device;
query a database storing a plurality of machine learning models that each predict a psychological risk value to determine whether one of the plurality of machine learning models predicts a psychological risk value associated with the user-set goal specified by the user of the first client device and received through the portion of the one or more of the user interface screens for entering text specifying the goal;
in response to determining that one of the plurality of machine learning models predicts the psychological risk value associated with the received goal, obtain two or more psychological risk values outputted by that machine learning model;
cause rendering on a second client device of a risk assessment interface generated for the user, wherein the risk assessment interface comprises a color coded risk assessment chart with a plurality of colors denoting successively increasing risk levels, and wherein the risk assessment interface renders an indicium indicating where on the risk assessment chart the user having specified the user-set goal is rated;
assess, by the assessment change module based on the two or more outputted psychological risk values, temporal changes in a real-time psychological risk value associated with the user-set goal specified by the user of the first client device and received through the portion of the one or more of the user interface screens for entering text specifying the goal
based on contact information specified in the portion of the one or more user interface screens, generate a dialog between the client device and the buddy system, with the dialog associated with the assessed temporal changes in the real-time psychological risk value associated with the goal;
execute an assistance processing module that comprises analysis objects that are persistent programming objects stored in a database on a computer hard drive of a server, comprising:
instantiating the analysis objects by initializing parameters and placing the analysis objects into memory of the server where they are executed;
post by the assistance processing module to the buddy system to a buddy system, the generated dialog;
track by the assistance processing module edits to the generated dialog made on the buddy system; and
at a time subsequent to the tracking of the changes, output, by the assistance processing module to the buddy system, another generated dialog with suggested text based on past edits, with past edits having been made more frequently being given more prominence in modifying suggested text than past edits being made less frequently.

10. The product of claim 9, wherein the instructions for causing the system to generate the dialog comprises instructions to generate the dialog correlated to wording appropriate to the assessed temporal changes in the psychological real-time risk value.

11. The product of claim 10, wherein the product further comprises instructions to:

receive the changes to the generated dialog; and track a count of the received changes to the generated dialog.

12. The product of claim 11, wherein the product further comprises instructions to:

adapt a subsequent generated dialog based on the count of the received changes made to the generated dialog.

13. An apparatus, comprising:

one or more processors;

a memory coupled to the one or more processors; and a computer-readable storage device storing a computer program product for mental state classification, the computer program product comprising instructions for causing the one or more processors to:

configure an assessment change module by:

causing rendering on a first client device of one or more user interface screens with a portion for entering text specifying a goal and another portion for specifying contact information of a buddy system, with the first client device being associated with a user;

execute the assessment change module, comprising instantiating analysis objects that are persistent programming objects stored in a database on a computer hard drive of a server by:

initializing parameters by a processor; and placing the analysis objects with initialized parameters into memory, where they are executed;

receive, through one or more of the rendered user interface screens of the assessment change module from the first client device over a network, a user-set goal that is specified by the user of the first client device;

query a database storing a plurality of machine learning models that each predict a psychological risk value to determine whether one of the plurality of machine learning models predicts a psychological risk value associated with the user-set goal specified by the user of the first client device and received through the portion of the one or more of the user interface screens for entering text specifying the goal;

in response to determining that one of the plurality of machine learning models predicts the psychological risk value associated with the received goal, obtain two or more psychological risk values outputted by that machine learning model;

cause rendering on a second client device of a risk assessment interface generated for the user, wherein the risk assessment interface comprises a color coded risk assessment chart with a plurality of colors denoting successively increasing risk levels, and wherein the risk assessment interface renders an indicium indicating where on the risk assessment chart the user having specified the user-set goal is rated;

assess, by the assessment change module based on the two or more outputted psychological risk values, temporal changes in a real-time psychological risk value associated with the user-set goal specified by the user of the first client device and received through the portion of the one or more of the user interface screens for entering text specifying the goal;

based on contact information specified in the portion of the one or more user interface screens, generate a dialog between the client device and the buddy system, with the dialog associated with the assessed temporal changes in the real-time psychological risk value associated with the goal;

execute an assistance processing module that comprises analysis objects that are persistent programming objects stored in a database on a computer hard drive of a server, comprising:

instantiating the analysis objects by initializing parameters and placing the analysis objects into memory of the server where they are executed;

post by the assistance processing module to the buddy system to a buddy system, the generated dialog;

track by the assistance processing module edits to the generated dialog made on the buddy system; and at a time subsequent to the tracking of the changes, output, by the assistance processing module to the buddy system, another generated dialog with suggested text based on past edits, with past edits having been made more frequently being given more prominence in modifying suggested text than past edits being made less frequently.

14. The apparatus of claim 13, wherein the instructions for causing the one or more processors to generate the dialog comprises instructions to generate the dialog correlated to wording appropriate to the assessed temporal changes in the psychological real-time risk value.

15. The apparatus of claim 14, wherein the computer program product further comprises instructions to:

receive the changes to the generated dialog; and track the received changes to the generated dialog.

16. The apparatus of claim 15, wherein the computer program product further comprises instructions to:

adapt a subsequent generated dialog based on the received changes made to the generated dialog.

17. The product of claim 9 wherein the one of the plurality of machine learning models is one or more of a mental health model, a suicidality classifier model, a suicide ideation classifier model, a losing weight model, or a saving money model.

18. The product of claim 9 wherein the instructions cause the system to generate, in response to determining there is no machine learning model in the plurality of machine learning models that predicts the psychological risk value associated with the received goal, a newly-generated machine learning model that predicts the psychological risk value associated with the received goal.

19. The apparatus of claim 13 wherein the one of the plurality of machine learning models is one or more of a mental health model, a suicidality classifier model, a suicide ideation classifier model, a losing weight model, or a saving money model.

20. The apparatus of claim 13 wherein the instructions cause the one or more processors to generate, in response to determining there is no machine learning model in the plurality of machine learning models that predicts the psychological risk value associated with the received goal, a newly-generated machine learning model that predicts the psychological risk value associated with the received goal.

* * * * *